United States Patent
Bratlie

(10) Patent No.: US 11,116,544 B2
(45) Date of Patent: *Sep. 14, 2021

(54) DEVICE FOR REMOVING AN ITEM IMPLANTED UNDERNEATH THE SKIN

(71) Applicant: REMOVAID AS, Oslo (NO)

(72) Inventor: Marte Bratlie, Oslo (NO)

(73) Assignee: REMOVAID AS, Oslo (NO)

( * ) Notice: Subject to any disclaimer, the term of this patent is extended or adjusted under 35 U.S.C. 154(b) by 314 days.

This patent is subject to a terminal disclaimer.

(21) Appl. No.: 16/378,630

(22) Filed: Apr. 9, 2019

(65) Prior Publication Data

US 2019/0274731 A1  Sep. 12, 2019

Related U.S. Application Data

(63) Continuation of application No. 14/115,048, filed as application No. PCT/EP2013/058236 on Apr. 19, 2013, now Pat. No. 10,314,617.

(30) Foreign Application Priority Data

Apr. 19, 2012 (GB) ................................. 1206878
Jan. 16, 2013 (GB) ................................. 1300815

(51) Int. Cl.
*A61B 17/50* (2006.01)
*A61B 17/30* (2006.01)
(Continued)

(52) U.S. Cl.
CPC ............. *A61B 17/50* (2013.01); *A61B 17/30* (2013.01); *A61F 6/18* (2013.01); *A61M 5/425* (2013.01)

(58) Field of Classification Search
CPC ..... A61M 37/0069; A61M 5/425; A61F 6/00; A61F 6/12; A61F 6/14; A61F 6/144;
(Continued)

(56) References Cited

U.S. PATENT DOCUMENTS

| 2,491,050 A | 12/1949 | Mcadoo |
| 3,010,455 A | 11/1961 | Cooper |

(Continued)

FOREIGN PATENT DOCUMENTS

| CN | 1767871 A | 5/2006 |
| CN | 201987725 U | 9/2011 |
| WO | WO 2007/024995 A2 | 3/2007 |

OTHER PUBLICATIONS

Search Report from corresponding application No. GB1307156.8, filed Apr. 19, 2013, assigned to REMOVAID AS.
(Continued)

*Primary Examiner* — Richard G Louis
(74) *Attorney, Agent, or Firm* — Saliwanchik, Lloyd & Eisenschenk

(57) ABSTRACT

A tool for use in fixing the position of an implanted item beneath skin, comprises:
a main body,
a channel in the main body, the channel defining at least two gripping interfaces for engagement with the skin and around the implanted item,
wherein the interfaces are positioned such that, when engaged with the skin, the interfaces retain the implanted item in a known position relative to the engaged skin.
Methods of using the tool are also described.

10 Claims, 17 Drawing Sheets

(51) Int. Cl.
 *A61M 5/42* (2006.01)
 *A61F 6/18* (2006.01)

(58) Field of Classification Search
 CPC ...... A61F 6/146; A61F 6/18; A61B 17/32093; A61B 17/30; A61B 17/50
 See application file for complete search history.

(56) References Cited

U.S. PATENT DOCUMENTS

| | | | |
|---|---|---|---|
| 3,880,156 A * | 4/1975 | Hoff | A61F 6/18 |
| | | | 128/840 |
| 4,269,190 A | 5/1981 | Behne | |
| 4,314,568 A | 2/1982 | Loving | |
| 4,438,770 A | 3/1984 | Unger et al. | |
| 4,724,832 A * | 2/1988 | Strubel | A61F 6/144 |
| | | | 128/840 |
| 4,753,636 A | 6/1988 | Free | |
| 5,064,429 A | 11/1991 | Waterman et al. | |
| 5,147,306 A | 9/1992 | Gubich | |
| 5,242,453 A | 9/1993 | Gubich | |
| 5,620,419 A | 4/1997 | Liu et al. | |
| 5,797,954 A | 8/1998 | Shaffer et al. | |
| 6,412,639 B1 | 7/2002 | Hickey | |
| 6,767,003 B1 | 7/2004 | Toensing | |
| 7,090,196 B1 | 8/2006 | Linker | |
| 7,799,042 B2 | 9/2010 | Williamson et al. | |
| 8,074,857 B2 | 12/2011 | Peterson et al. | |
| 2002/0095122 A1 | 7/2002 | Shaffer | |
| 2004/0049251 A1 | 3/2004 | Knowlton | |
| 2007/0233184 A1 * | 10/2007 | Wong | A61B 17/7083 |
| | | | 606/205 |
| 2009/0099403 A1 | 4/2009 | Zimmerling et al. | |
| 2009/0105608 A1 | 4/2009 | Chiu et al. | |
| 2014/0236162 A1 | 8/2014 | Barongan | |

OTHER PUBLICATIONS

Kanduyil, V. N. "Easy Method for Implanon Removal," *J Fam Plann Reprod Health Care*, 2012, pp. 207-208, vol. 38, No. 3.

\* cited by examiner

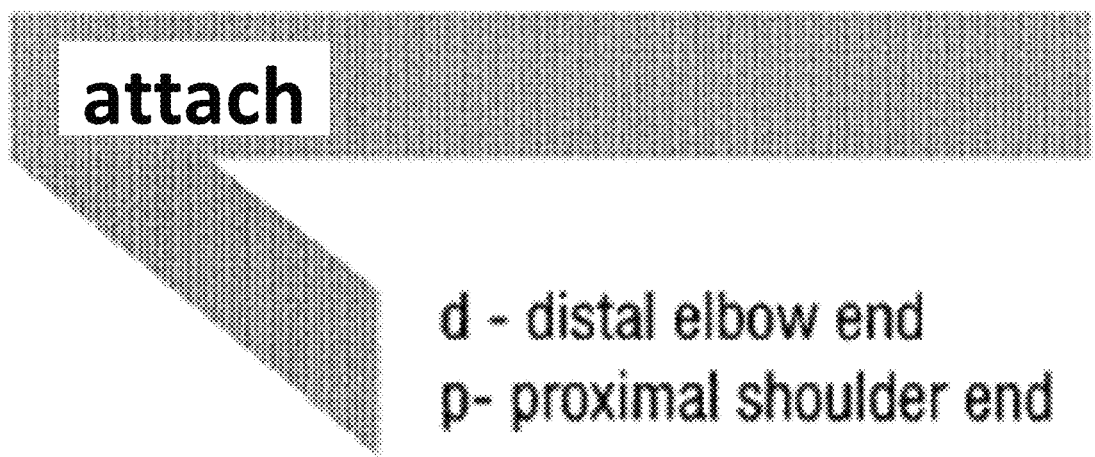
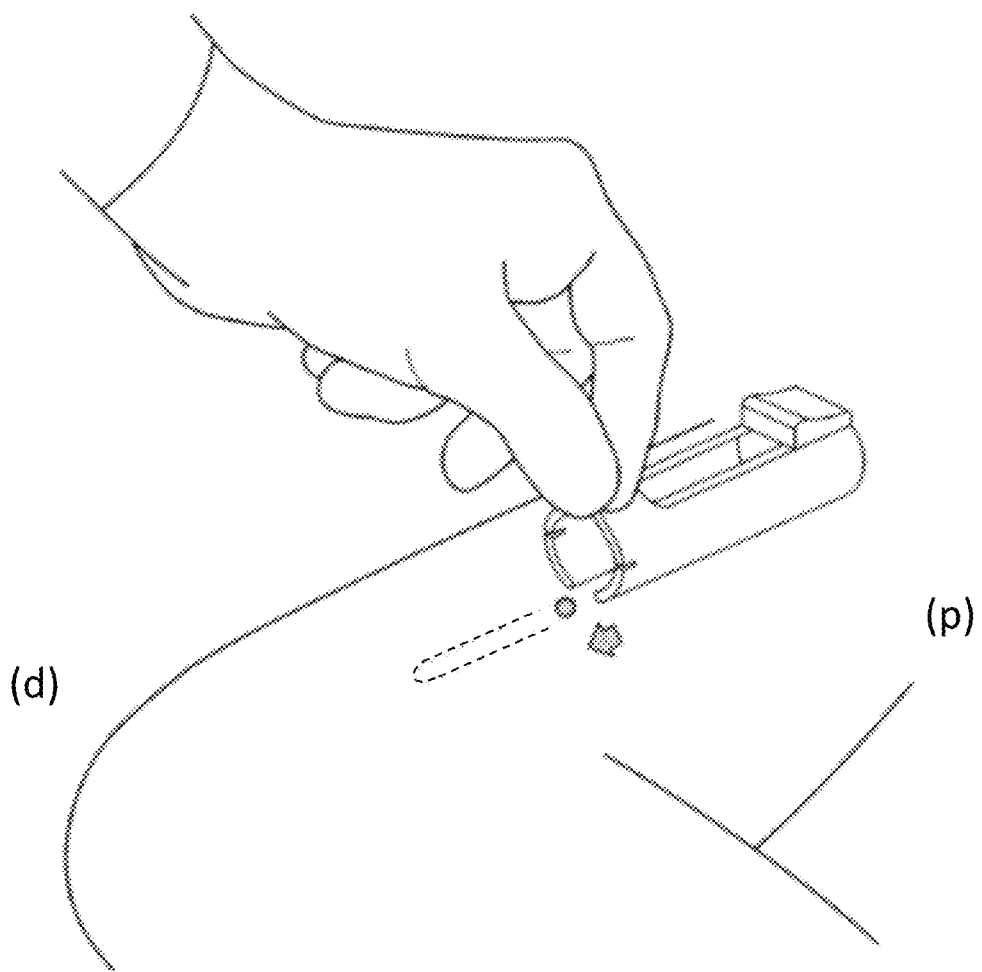
FIG. 1B

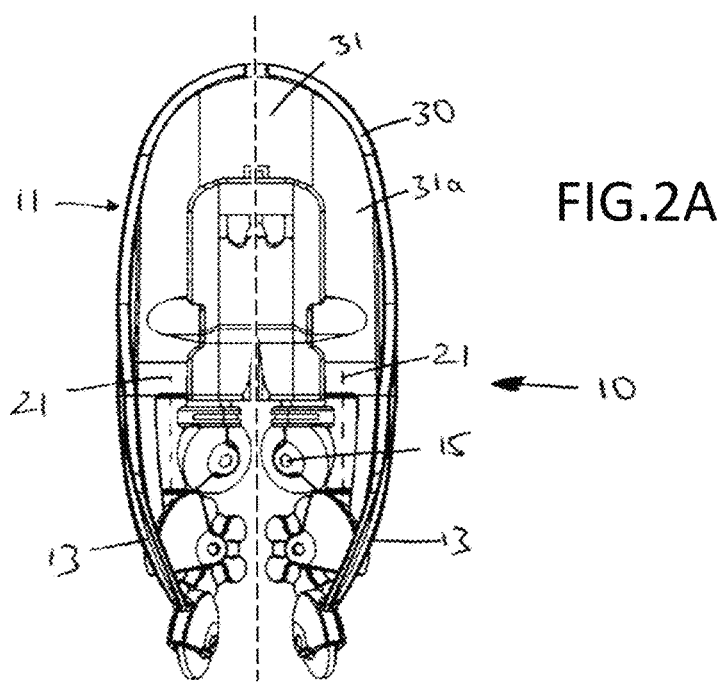
FIG.2A
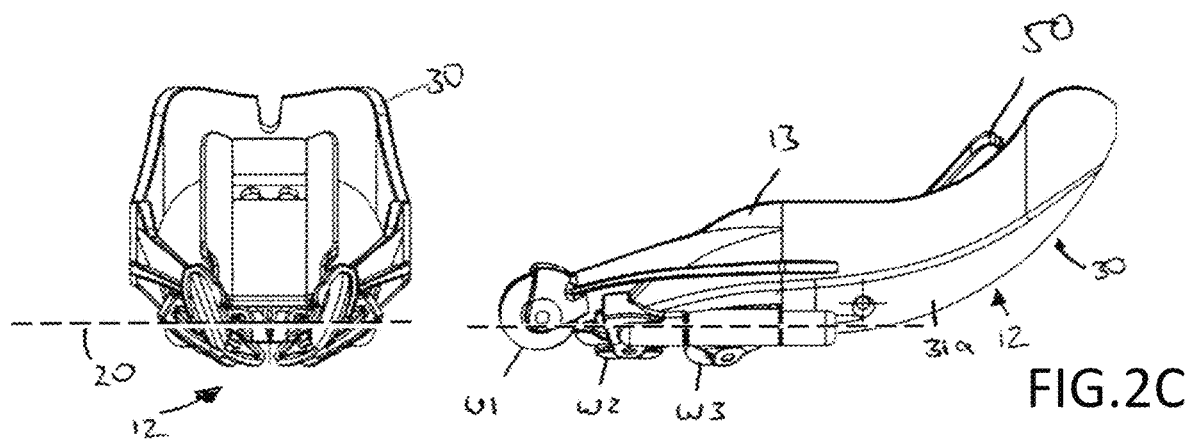
FIG.2B
FIG.2C
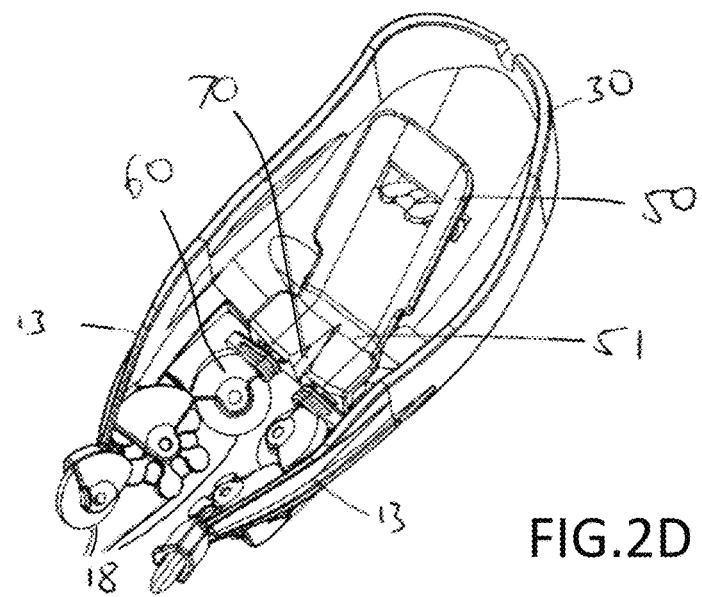
FIG.2D

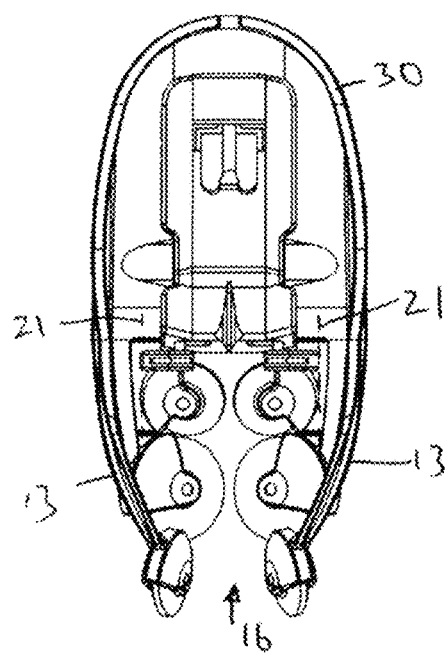
FIG. 3A
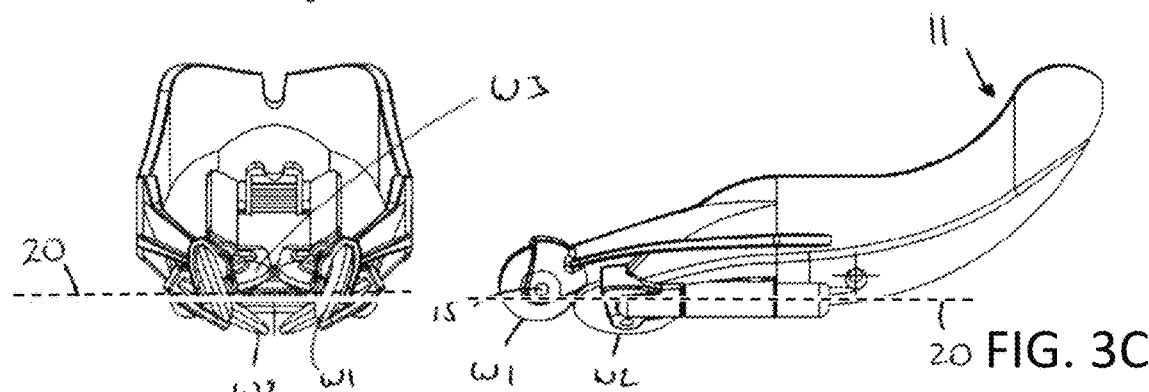
FIG. 3B
FIG. 3C
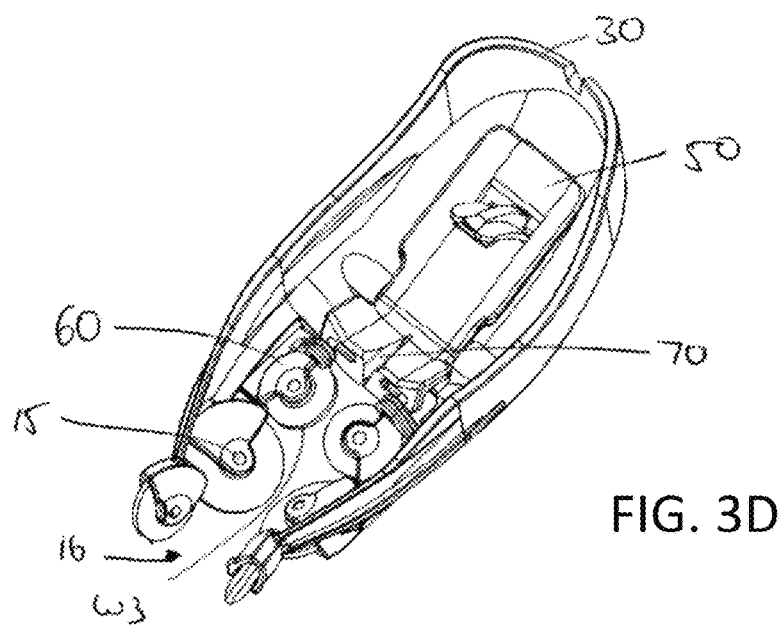
FIG. 3D

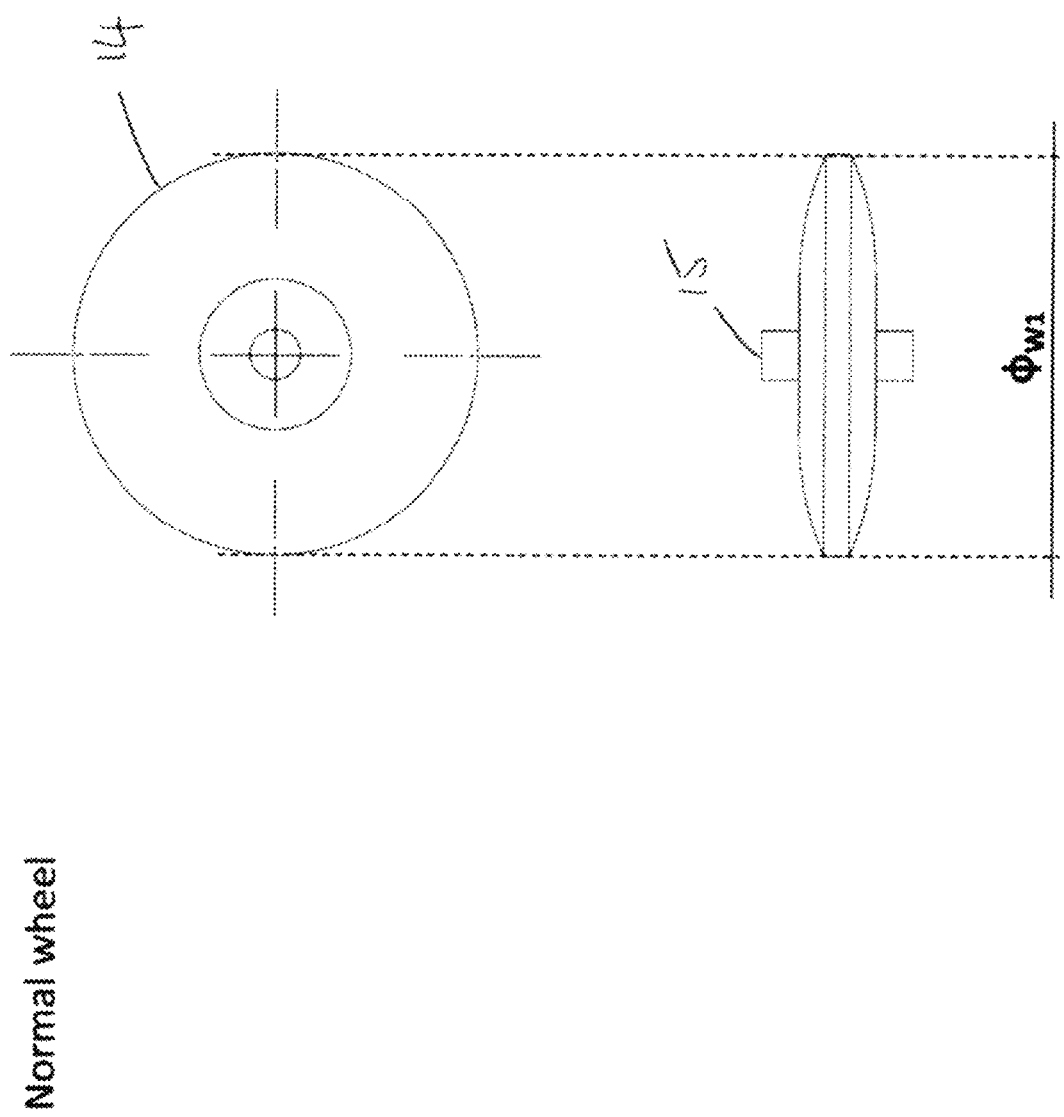

Step 1
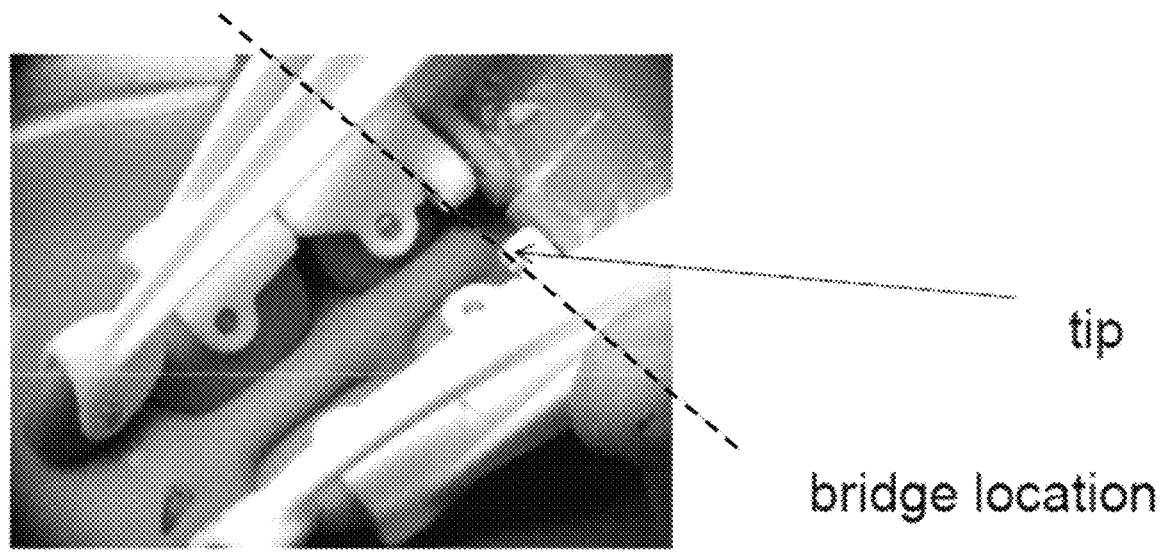
tip
bridge location
Step 2
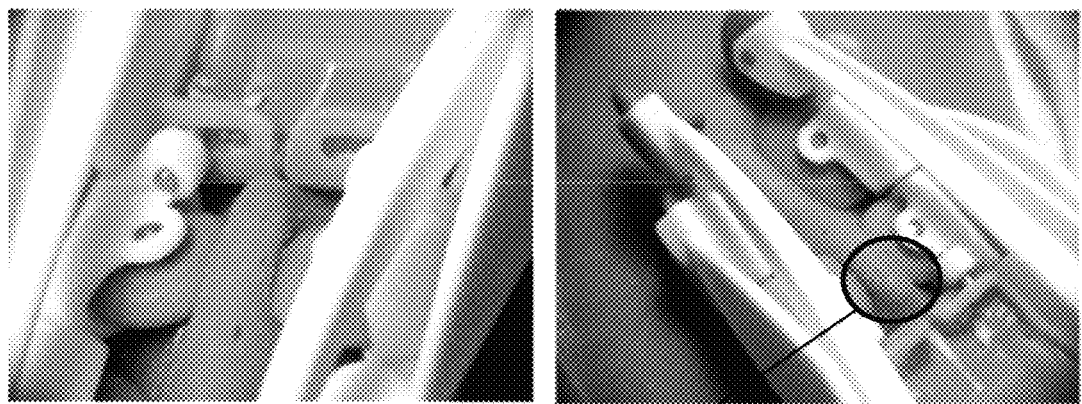
gap between wheels is reduced → the implant is secured in raised position
target area is lifted and exposed
FIG. 8A Step 3
Use slot as a guidance for needle positioning
Step 4
Incise target area by using a scalpel blade
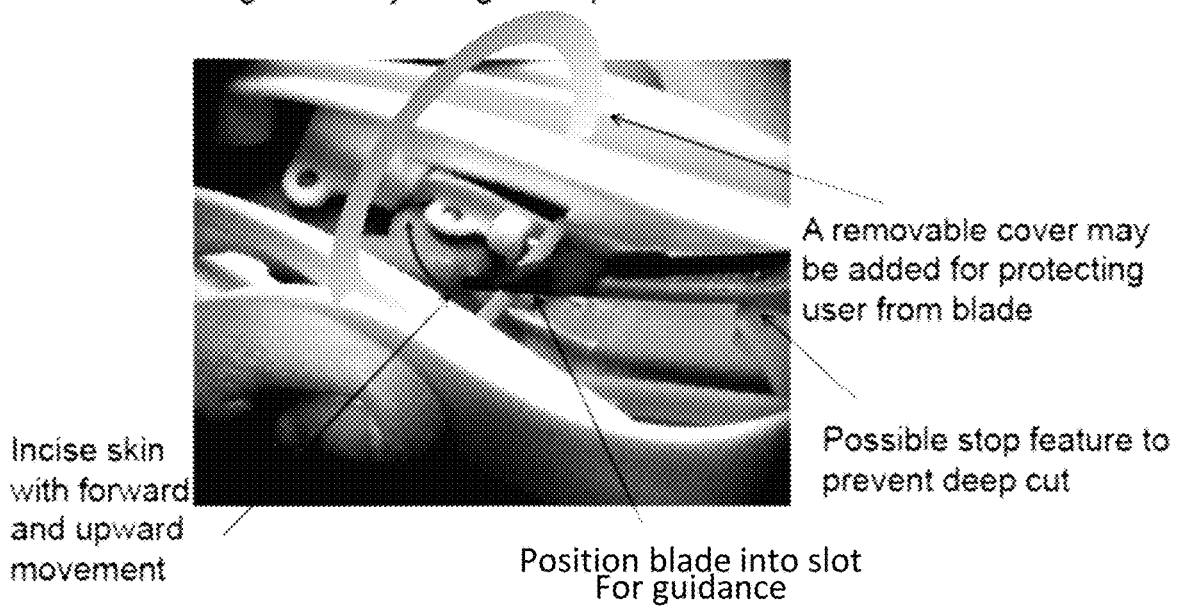
Incise skin with forward and upward movement
A removable cover may be added for protecting user from blade
Possible stop feature to prevent deep cut
Position blade into slot for guidance
FIG. 8B Step 5

Implant should protrude from stretched cut skin

Extraction should not require excessive force if fibrin sheet has been cut

DEVICE FOR REMOVING AN ITEM IMPLANTED UNDERNEATH THE SKIN

CROSS REFERENCE TO RELATED APPLICATIONS

This application is a continuation of U.S. application Ser. No. 14/115,048, filed Oct. 31, 2013, which is the National Stage Application of International Application Number PCT/EP2013/058236, filed Apr. 19, 2013; which claims priority to Great Britain Application No. 1206878.9, filed Apr. 19, 2012 and Great Britain Application No. 1300815.6, filed Jan. 16, 2013; all of which are incorporated herein by reference in their entirety.

FIELD OF THE INVENTION

This invention relates to a tool intended for use in a surgical procedure.

BACKGROUND OF THE INVENTION

There is an increasing use of long-term contraceptives, of which one type is a subdermal implant in the form of a rod that releases contraceptive hormone, until it needs to be removed or replaced with a new rod. For example, Nexplanon [Schering-Plough Limited/Merck, Sharp & Dohme Limited (MSD) US] is a subdermal implant indicated for use as a long-term contraceptive for women. It entered the European market in 2010, replacing Implanon (available in Europe and SE Asia since 1998, and approved in the US in 2006), the most widely used implantation system in the world, marketed in 32 or more countries throughout the world. The implant of both Implanon and Nexplanon is a 4 cm long, 2 mm diameter non-biodegradable ethylene vinyl acetate (EVA) copolymer core, containing 68 mg of the synthetic progestin etonogestrel, surrounded by a rate-controlling EVA copolymer membrane. The implant must be replaced or removed 3 years after insertion.

Other contraceptive implants are Jadelle, 43 mm long, 2.5 mm diameter (2 rods), lasts 5 yrs, and Sino-Implant II, 44 mm long, 2.4 mm diameter (2 rods), lasts 4 yrs.

Increased focus on the benefits of long-acting, reversible contraception has spurred an increase in CI insertions in recent years, both in industrialised and developing countries. On a global scale, multiple campaigns have been launched to meet UN Millenium Goals 4 and 5, i.e. reduction of maternal and child mortality, and a steep increase in CI procurement is expected for the foreseeable future. Within few years millions of women will need to have their CIs removed on an annual basis.

Since CIs were introduced to the commercial market in the early 1980s, implant manufacturers have focused intense efforts on making insertion of CIs easier. For instance, a unique, preloaded disposable applicator developed for Nexplanon ensures "fail proof" and efficient subdermal insertion of the implant. CI removals, on the other hand, have largely been left untouched and at the mercy of the various service providers. The CI removal procedure recommendations have remained essentially unchanged for 40 years, relying on general surgical skills from the service provider.

While contraceptive implant (CI) insertion is easily managed through the use of specialsed introducer trocars, CI removal is a complex task that requires specialist training. There exists no standardised method for CI removal, and no dedicated removal devices are available on the global market. Currently, CIs are 1-5 removed using scalpels and forceps and rely on the general surgical skills of the service provider. Thus, the procedure is highly variable in duration and often cumbersome, both for the patient and for the clinician. The complex current CI removal procedure is a major impediment to a desired increase of CI use. Introducing a simple, safe and effective CI removal procedure could improve patient care, be cost-effective for CI service providers and increase access to complete CI care.

All available research shows that the procedure length of the current CI removal procedure is highly variable and heavily reliant on individual operator skills.

SUMMARY OF THE INVENTION

The present invention aims to simplify the removal process of an implanted item that is positioned/implanted under the skin (e.g. subdermally or subcutaneously), in particular a contraceptive implant such as those described above, or other pharmaceutical subdermal or subcutaneous implants. Usually, such implants cannot be visually located when in use, and may be difficult to locate by touch. A tool of the invention aids the removal by fixing the position of the implant, in particular the area of the implant near where an incision is to be made, prior to making an incision in the skin, thereby abolishing the need to re-locate the implant under the skin after the incision is made.

In summary, the present invention seeks to ameliorate inter-operator variability and reduce procedural complexity by radically changing the CI removal procedure. A tool of the invention seeks to standardise the removal of a foreign body, reduce the time taken to remove a foreign body, and minimise the damage to the skin and surrounding tissue on removal of the foreign body.

According to a first aspect, the present invention is a tool for use in fixing the position of an implanted item beneath skin, the tool comprising:
a main body,
a channel in the main body, the channel defining at least two gripping interfaces for engagement with the skin and around the implanted item,
wherein the interfaces are positioned such that, when engaged with the skin, the interfaces retain the implanted item in a known position relative to the engaged skin.

According to a second aspect, the present invention is a sterile kit comprising a tool as defined above.

According to a third aspect, the present invention is a method of removing an item implanted under the skin, which comprises fitting a device around at least part of the item and the overlying skin, making a surgical incision near to an end of the item, and removing the item through the incision.

According to a fourth aspect of the present invention, a device is provided for assisting the removal of a foreign body positioned under the skin, the device comprising non-invasive means for stretching the skin over at least part of the foreign body, and to fix the position of the foreign body in relation to the overlying skin, such that the point of incision can be determined.

The invention provides a device (disposable and/or multi-use) to fixate a subdermal and/or subcutaneous foreign body in relation to the overlying skin, and/or to aid longitudinal and/or centralised movement of the implant.

BRIEF DESCRIPTION OF THE DRAWINGS

FIGS. 1A-1F illustrate one embodiment of an implant removal tool and steps for using the implant removal tool to remove an implant from beneath the skin.

FIGS. 2A-2D illustrate a top, front, side, and perspective view, respectively, of an alternative embodiment of an implant removal tool.

FIGS. 3A-3D illustrate a top, front, side, and perspective view, respectively, another alternative embodiment of an implant removal.

FIG. 6 is an enlarged top view of the implant removal tool in FIG. 2a.

FIG. 7 is an enlarged top view and side view of a wheel used with an embodiment of an implant removal tool.

FIGS. 8A-8C illustrate the steps for removing an implant from under the skin using an embodiment of an implant removal tool.

DESCRIPTION OF PREFERRED EMBODIMENTS

Figure 1A:
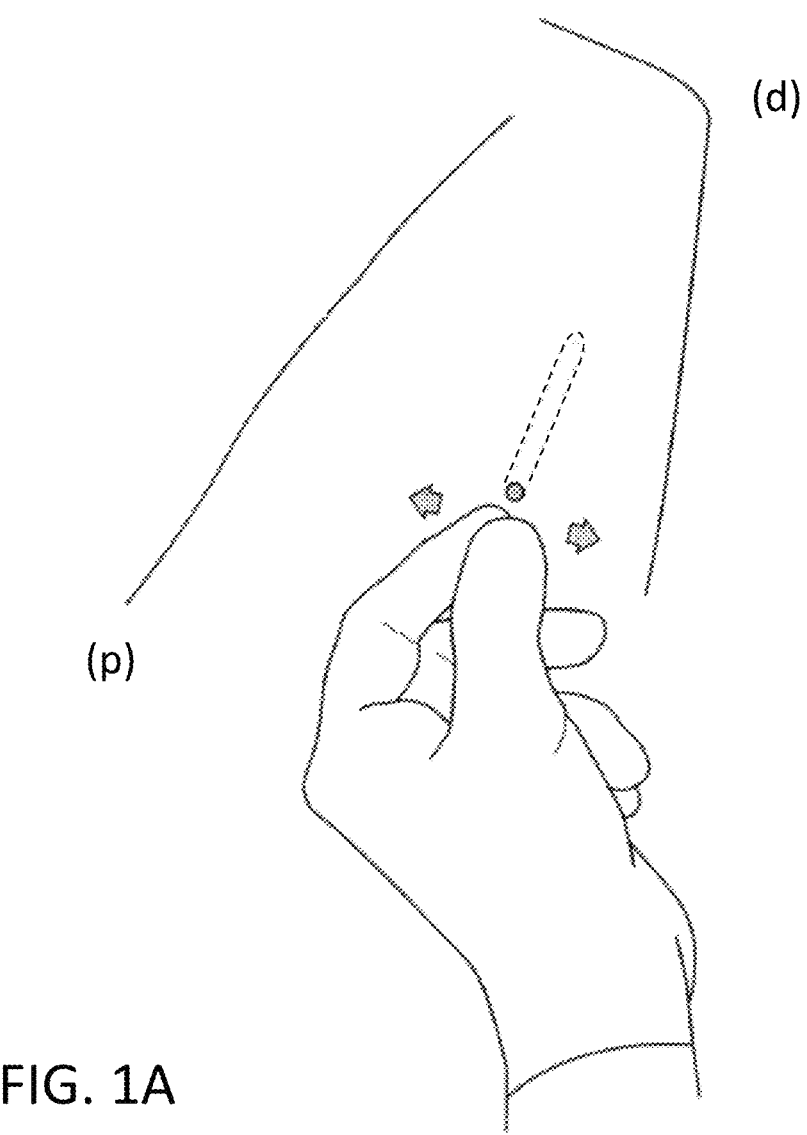

A device of the invention may be single use, i.e. disposable, or it may be capable of being used multiple times.

The terms "implant", "foreign body" and "implanted item" are used herein interchangeably.

A device of the invention may be used to remove a single foreign body positioned under the skin. It may also be used to remove more than one, e.g. 2, 3 or 4 foreign bodies at the same time (or successively).

The foreign body that is positioned under the skin may be any medical subdermal or subcutaneous implant or e.g a microchip. Preferably it is a contraceptive implant. More preferably, it is elongate. Most preferably, it is rod-shaped.

A device of the invention stretches the skin and fixes the position of the foreign body, such that the point of incision can be determined. This means that the device enables the position of the foreign body to be located by visual and/or tactile means. Preferably, the device will make the foreign body palpable by a person and/or enable it to be visualised. Alternatively, the device may cover the point of incision, but the fact that the skin is stretched and the position of at least part of the foreign body is fixed, means that the device can be used to determine the correct position for the incision.

Preferably, the device will position the foreign body such that it can be visualised by a person (i.e. the person removing the foreign body). The foreign body may be made more clearly visible by applying gentle pressure to a part of the foreign body. In the embodiment where the foreign body is a contraceptive rod-shaped implant, then the application of pressure to one end may improve the visibility of the other end of the implant.

A device of the invention may be used to aid removal of an implant. In a preferred embodiment, the person removing the implant tilts the implant by applying a downward/forward pressure/force near and/or upon one end of the implant, to force the other end of the implant in the direction of the overlying skin. This may cause the implant to protrude slightly on the surface of the skin, or at least enable the implant to be located more easily. In addition, or alternatively, the device itself may be used to apply the downward/forward pressure to one end of the implant. Once the item can be located, the skin that lies over the end of the implant that is nearest to the surface of the skin is stretched, and that end of the implant is secured, in relation to the overlying skin. This enables a person (or the device) to determine where a surgical incision should be made.

In a preferred embodiment, a part of the device is positioned underneath at least part of the implant, in order to stretch the skin and/or secure the tip of the implant. The device may be adapted to prevent the tip of the implant from "falling back" into the skin and thus the correct position of the incision can easily be determined, and the foreign body/implant does not need to be located again after the incision has been made.

The principle of the invention is to secure the position of the implant relative to the overlying skin and to stretch the skin over one end of the implant (the end that is intended to be removed first). This enables a person (or the device) to determine the point of incision. The device is also configured to ensure that once the incision has been made, the implant does not "fall back" into the skin. Preferably, the principle of operation of the device is to:

1) Act on a part of the foreign body in order to force the foreign body in the direction of the overlying skin. This may be in the form of a "tilting" motion.

2) Secure the "tilted" end/tip of the foreign body whilst retaining the "tilting" of the tip through mechanisms integral to the device, so that it does not "fall back" into the skin and can be located by the person removing the foreign body. A person is then able to make a surgical incision at the correct point. Alternatively, the device may comprise integral incision means (e.g. a scalpel), for making the incision.

3) Secure the foreign body in relation to the overlying skin, preferably by clamping around a portion of skin containing the foreign body. Steps 2 and 3 may be accomplished in one single action.

In a preferred embodiment, a device of the invention comprises an elongate slot, or can be manipulated/configured, in use, to form a slot, with wheels at each side of the slot, such that the device can roll along the surface of the skin and cause a fold of skin containing at least a part of the foreign body to protrude through the slot. The configuration of the elongate slot also enables the device to stretch the skin over the first end of the foreign body and to secure the first end in relation to the overlying skin, such that an incision can be made near to the first end of the foreign body.

In order that it should be suitable for use in a surgical procedure, a device of the invention will typically be provided in a sterile package. Suitable materials and sterilising techniques are known to those of ordinary skill in the art.

The internal diameter of the device, or in the internal diameter of the channel that is defined by engagement interfaces, may vary, depending on the patient on which the device is to be used on. For example, the device may have to be adapted depending on the individual, and the amount of subcutaneous fat that they carry on their arms. These are routine modifications, within the knowledge of the skilled person.

The channel that is defined by the engagement interfaces may be open at both ends, open at one end and closed at one end, or it may be closed at both ends.

The channel preferably has a discontinuous circumference, i.e. is open longitudinally. The channel is preferably pre-formed in the main body of the tool. However, it may be formed "in use", i.e. when engaging the skin.

By comparison with the prior art, the present invention standardises the procedure, allowing for less inter-clinician variability in technique; it will increase efficiency both by reducing the need for clinician training and by shortening the procedure time. In addition it will reduce scarring; in particular, the ability to make more precise incisions should result in smaller/less scarring. Further, securing the implant in place before the incision is made allows the incision to be made at the correct exit point.

Preferably, a tool/device of the invention comprises a scalpel, or other suitable means for making an incision in the skin. More preferably, a device of the invention includes an anaesthetic, for anaesthetising the skin before the incision is made.

In a preferred embodiment, an elongate, essentially tubular device of a resilient material is provided, the device comprising an elongate slot whereby the device can be fitted around a rod lying beneath the skin, the device further comprises a moveable member that can act on the rod and thereby cause it to move longitudinally.

Preferably, the essentially tubular device has an internal diameter of 5 to 50 mm.

In a preferred embodiment, a method of removing a subdermally or subcutaneously implanted rod, comprises fitting an essentially tubular device as defined above around the rod and surrounding skin, making a surgical incision near one end of the device, and moving the member such that the rod is caused to pass out of the body through the incision.

The invention will now be illustrated with reference to the accompanying drawings.

FIGS. 1A to 1F show a device according to the invention, incorporating the preferred feature of a moveable member that can act on the rod and thereby cause it to move longitudinally out through an incision. FIGS. 1A to 1F describe steps for using this device.

The steps for using the device comprise locating the rod, alternatively marking the ends of the implant (FIG. 1A).

FIG. 1B shows attaching the removal device onto the patient's arm, fitting it around the rod and sliding it distally until the back end/slide "catches" the rod on the proximal end.

Figure 1C:
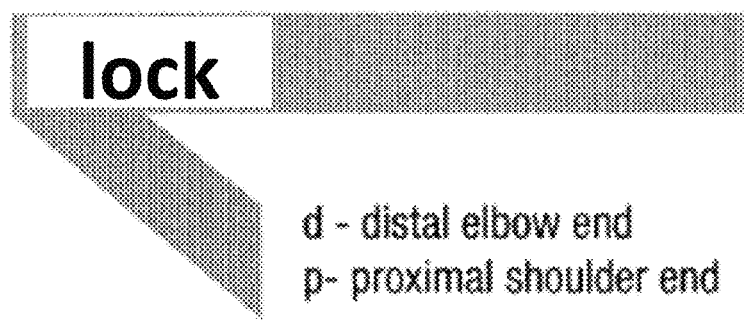

FIG. 1C shows the next step, which comprises the operator making sure they have placed the device in the correct position by sliding the plunger forward until the first "click" (stopping mechanism). The rod should now protrude under the skin in the centre of the distal opening of the device. This will lock the implant in place throughout the procedure.

Figure 1D:
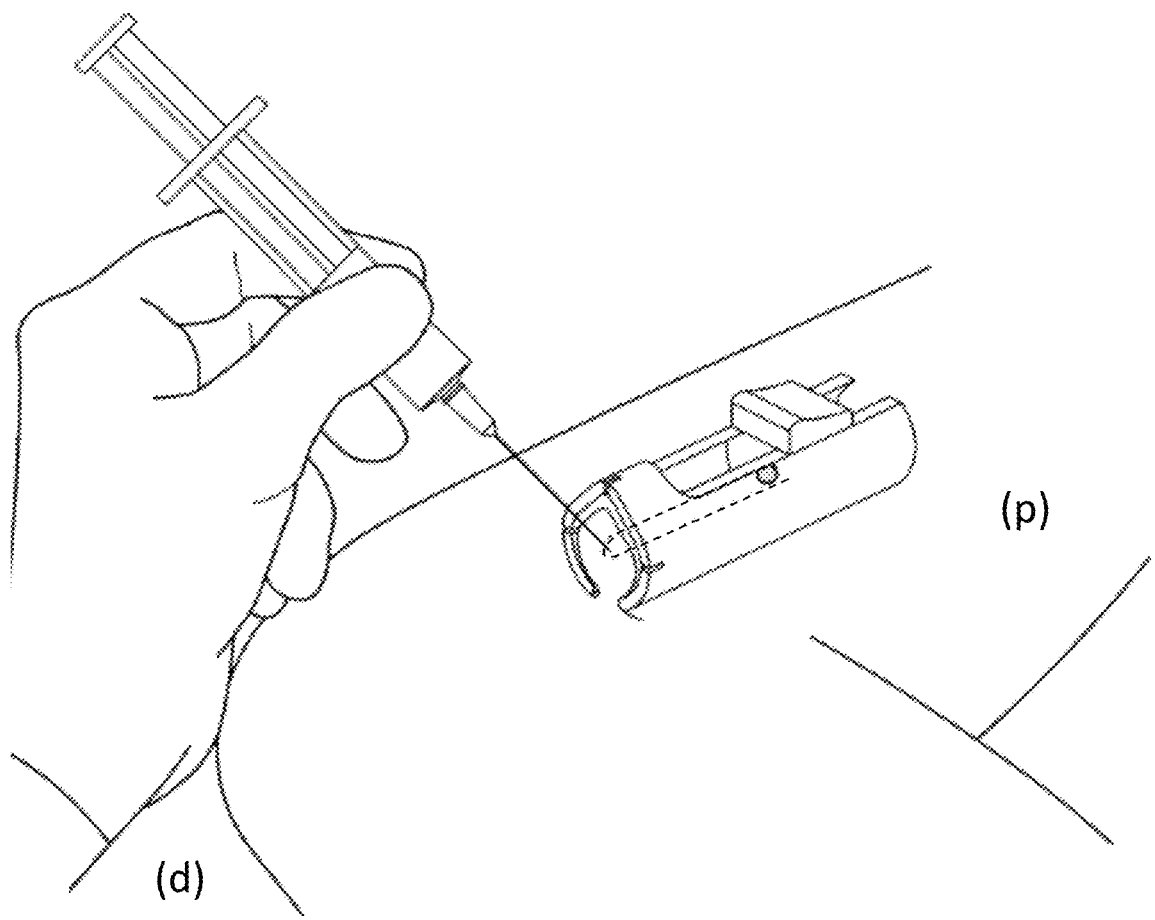

FIG. 1D shows the step of anaesthetising the area in the middle of the opening with, for example, lidocaine containing 1% adrenaline. A small amount (0.5 ml) should be more than sufficient (significantly reduced from the previous amount necessary, approx. 1-2 ml).

Figure 1E:
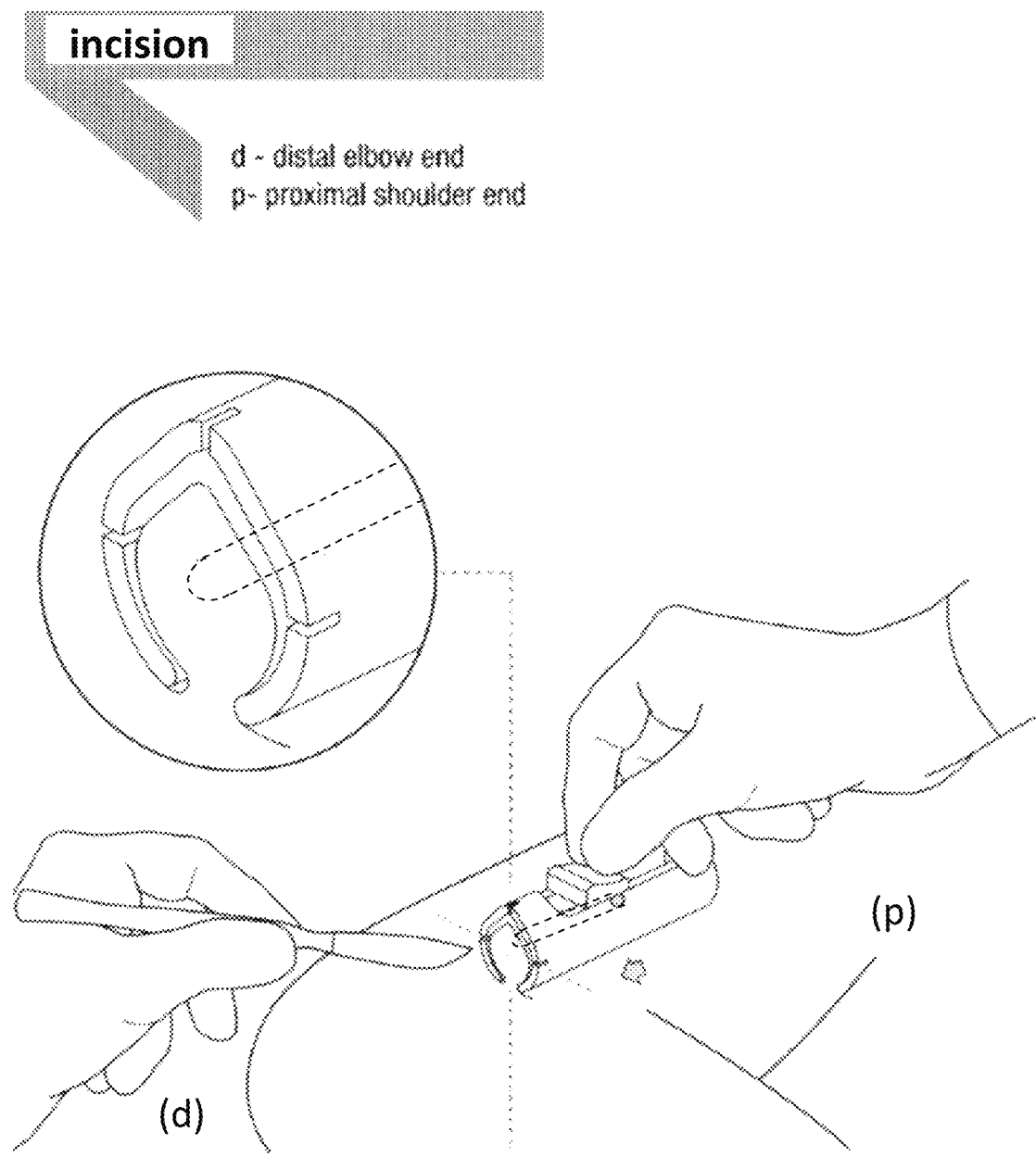

FIG. 1E illustrates the plunger being moved forward again until it "clicks" into the second step. Using a scalpel, the operator should make an incision by cutting inside the grooves in the device opening, which will only cut the skin immediately in front of the protruding rod.

Figure 1F:
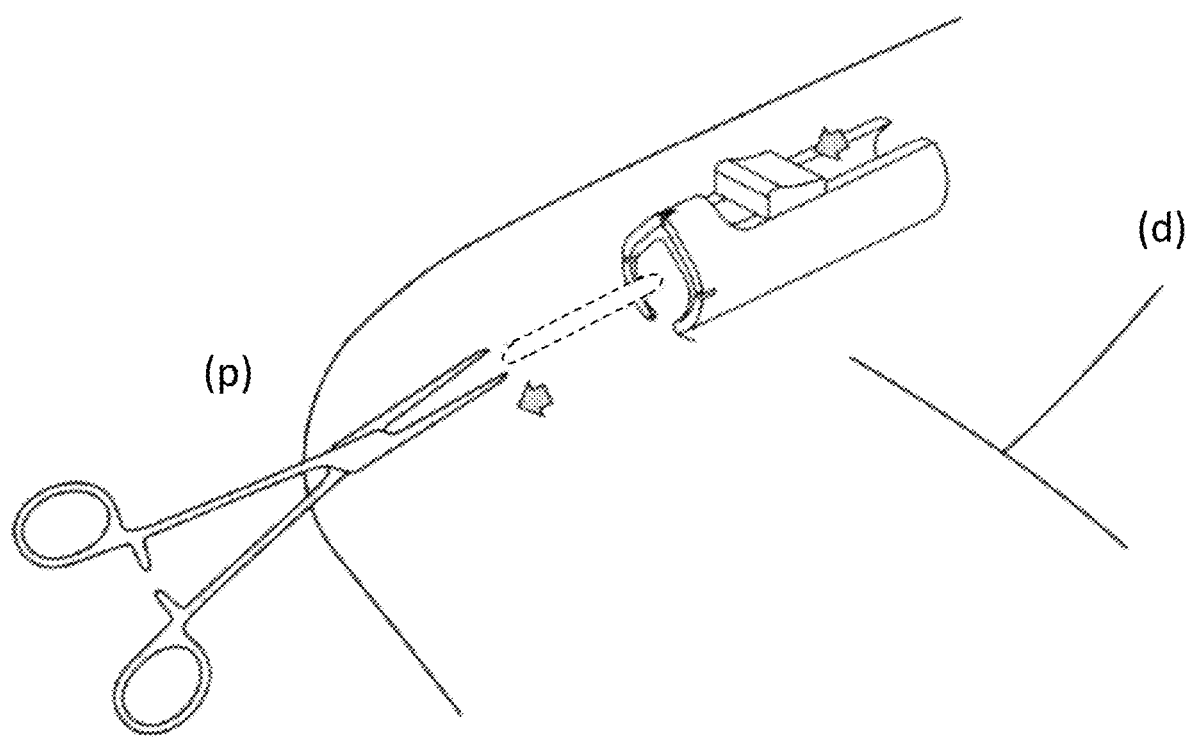
Figure 4:
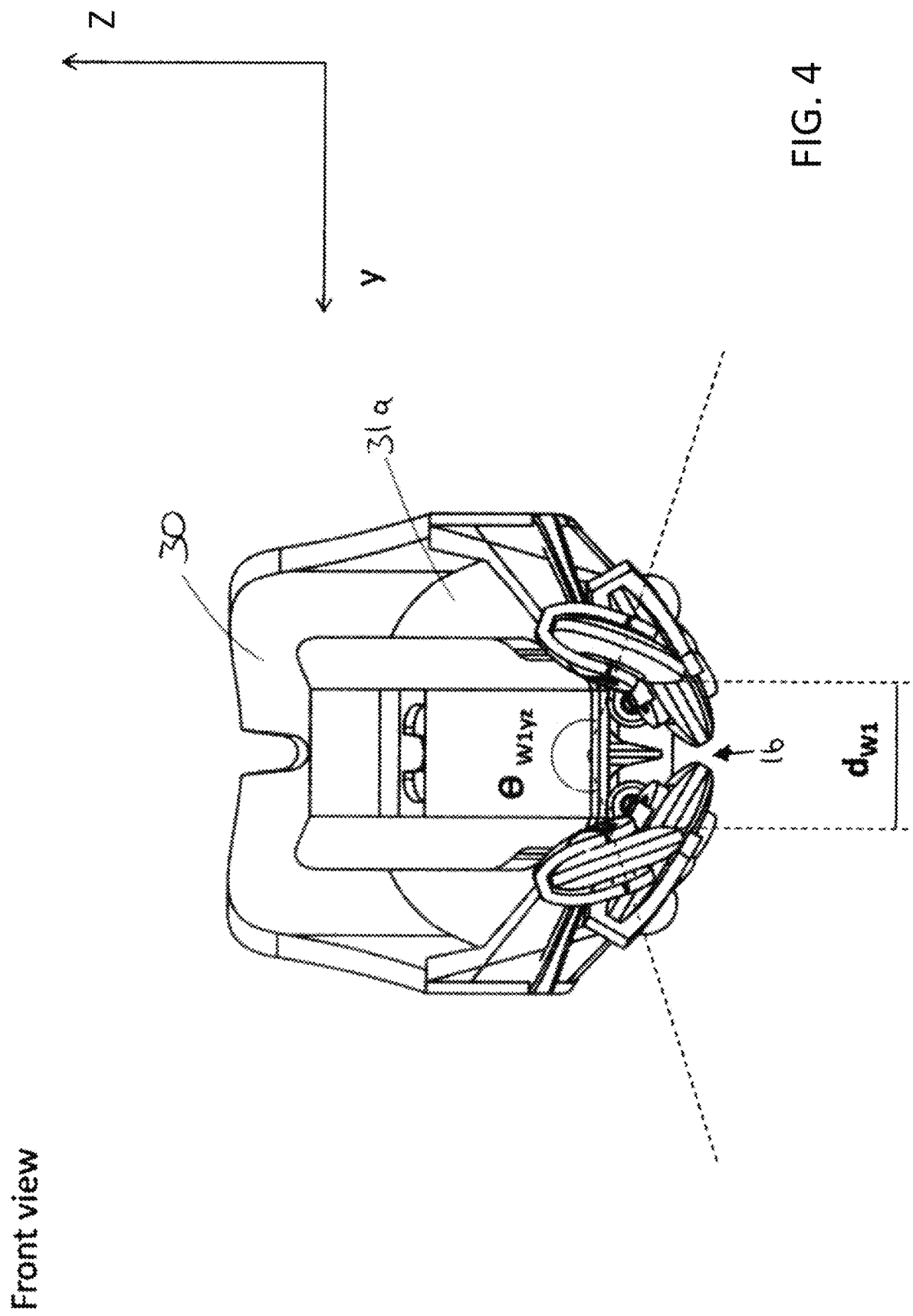
FIG. 4 is an enlarged front view of the implant removal tool in FIG. 2b
Figure 5:
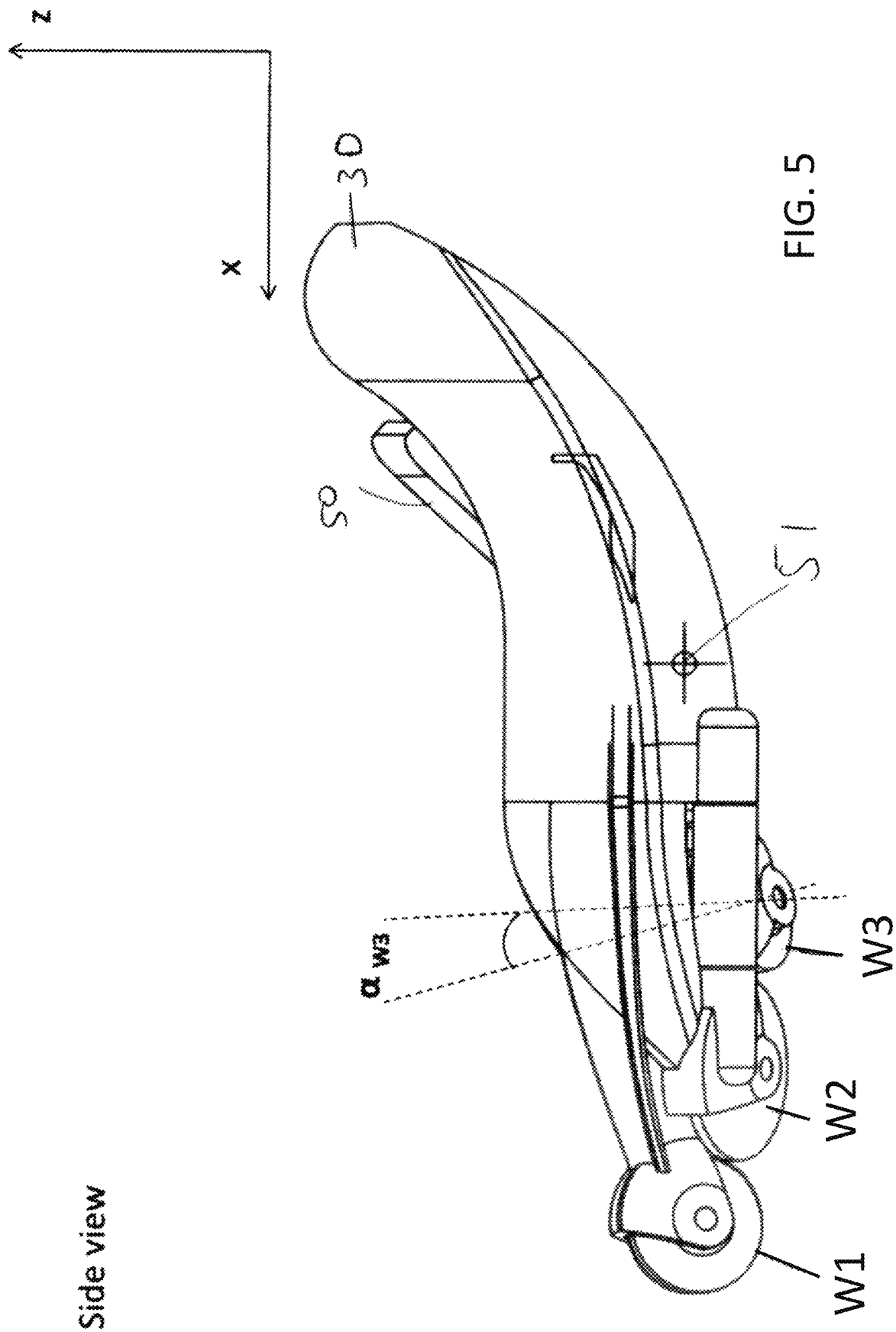
FIG. 5 is an enlarged side view of the implant removal tool in FIG. 2c.
Figure 6:
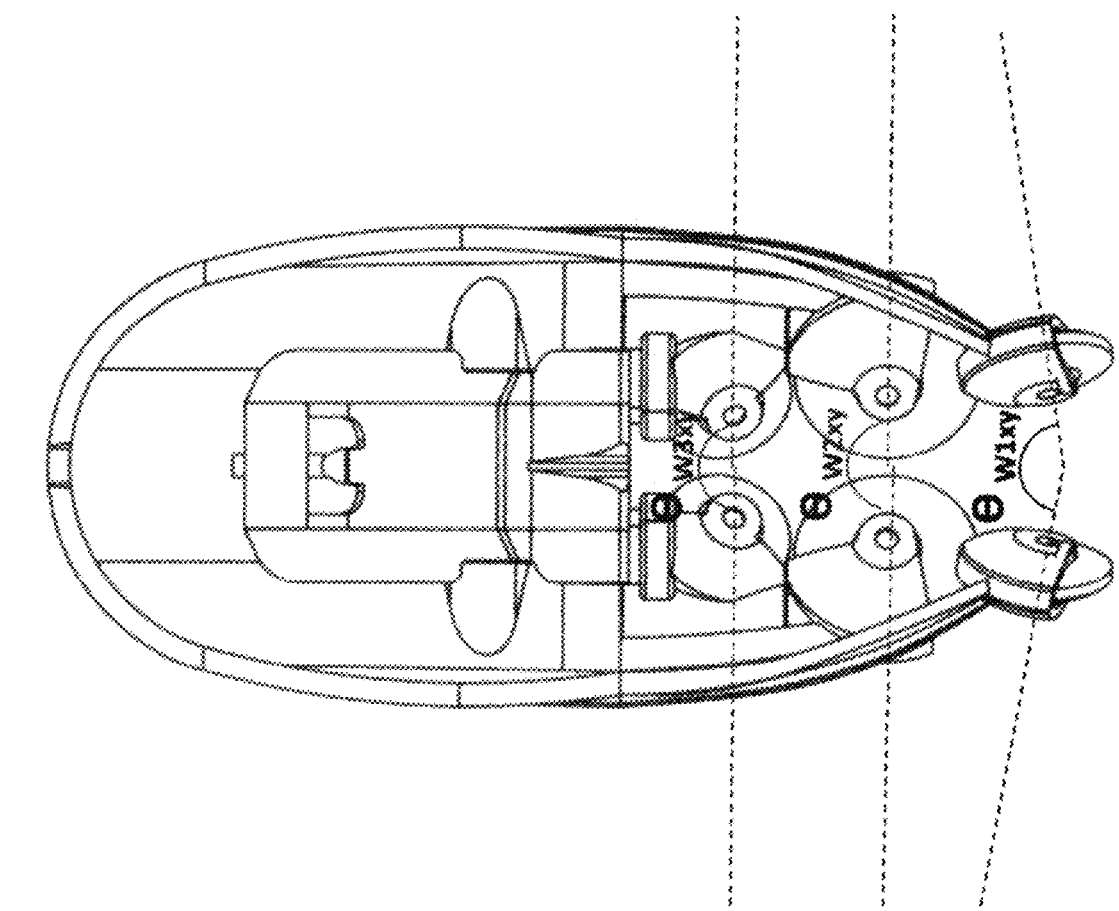

In FIG. 1F, the removal procedure is shown. The rod should now spontaneously protrude through the incision. The operator should remove the rod completely by sliding the plunger past the "clicking" point to push it forward. The rod can now easily be removed, and it will leave a very small incision—which again will leave a significantly smaller scar than in the techniques of the prior art.

Typical dimensions of a device according to FIGS. 1A to 1F, i.e. incorporating the preferred feature of a moveable member that can act on the rod and thereby cause it to move longitudinally out through an incision are a length of 30 to 80 mm; the internal diameter is, for example, at least 5, preferably at least 10, 20, 25 or 30 mm, and usually up to 25, 30, 40 or 50 mm. The internal diameter allows for a fold of skin to be placed within the device while one or more foreign bodies, e.g. as described above, is beneath the skin. The external dimensions will depend on the materials used.

Figure 8C:
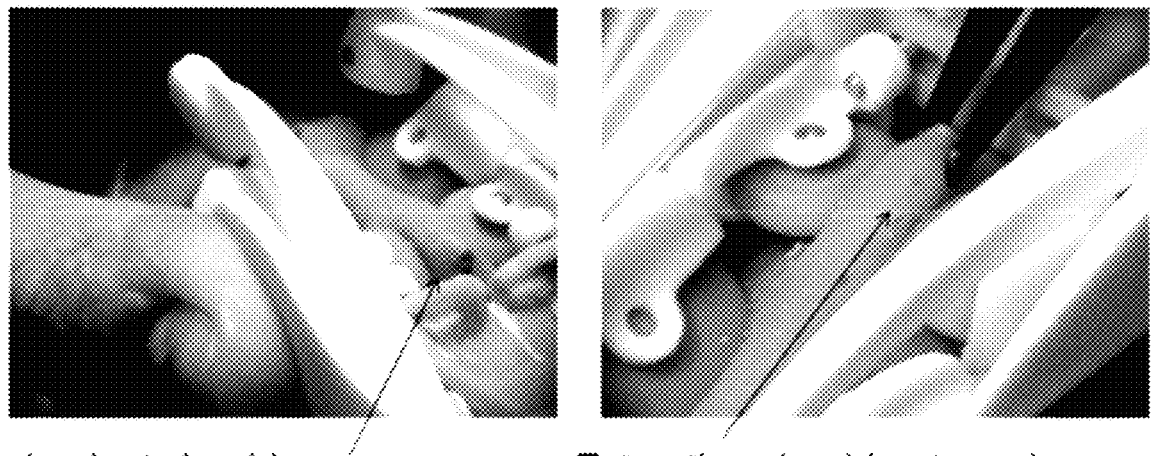

FIGS. 8A-8C illustrate another tool according to the present invention, and describes steps for using it. The tool is described in more detail with reference to FIG. 2A to 7.

In a first step, a tool is rolled onto the implant until the tip of the implant is positioned near the closed end of a channel and/or the device cannot be easily rolled further.

In a second step, the back wheels are raised and locked to lift the tip of the implant and expose the area to be incised.

In a third step, local anaesthetic is injected into the target area.

In a fourth step, the tip is located and an incision is made at the tip of the implant, In a fifth step, the implant is identified and extracted using surgical forceps.

FIGS. 2A to 2D and FIGS. 3A to 3D show a first example of a tool according to the present invention. Alternative examples are shown in later Figures, in particular in FIGS. 9 and 10.

A tool 10 is shown having a main body 11 having a lower surface 12 which, in use, contacts the skin of the human or animal in which the implant is located. Main body 11 comprises a substantially upstanding wall portion 30 extending from a base section made up of a central portion 31 and a pair of wing portions 31a. The base could be formed as a single section. The base may blend smoothly into the upstanding portion 30 or may have a defined edge.

The base section is curved both along a longitudinal axis 32 of the tool 10, but is also curved in a direction extending away from the longitudinal axis. Section 31 is joined, at least in part, to upstanding portion 30 by way of wing portions 31a. Elements 30, 31 and 31a define a hollow shell surrounding an open recessed portion.

The main body 11 is provided with a pair of arms 13 extending away from the main body and defining a channel 16 therebetween. On each arm, a plurality of discrete elements 14 are provided. In this example, the elements take the form of rotatable wheels (W1, W2, W3) which are rotatable about respective axes 15. The edges of wheels W1, W2 W3 provide an interface 18 associated with each arm such that, in use, the edges of the wheels are used to hold an implanted item in position, typically by pinching the skin around the implanted item. This is described in greater detail with reference to FIGS. 8A to 8C.

In an alternative, the interface 18 could be provided by way of a single element, for example a rigid surface or a belt looped around pulleys, rotating spheres or even by way of a series of finger type elements.

In this example, the channel 16 is open at one end. The channel is preferably elongate as shown. The channel preferably extends longitudinally from an inner portion of the main body towards an edge thereof. Thus, in use, the channel lies along and/or in contact with the skin, such that the "length" of the channel is substantially parallel to the surface of the skin. The channel may, as in this example, be closed at one end, i.e. at one longitudinal extreme of the channel. Alternative configurations are envisaged in which the channel is closed at both ends and does not have an open end. The width of the channel 16 is not constant in this example. In particular, the gap between wheels \A11 is larger than the gap between wheels W2 and W3. Typically, the width of the channel reduces from one end to the other end, to leave from the open end to the closed end. It may, however, be that the gap between wheels W3 is larger than the gap between wheels W2.

The arms 13 are preferably flexible, due to the material from which they are made, and also are preferably resilient such that the width of the channel 16 can be altered during use, but that the arms will apply a restoring force on one or more of wheels W1, W2 and W3 such that the wheels grip on either side of a pinched section of skin around or below an implanted item.

Each arm 13 may be formed as a single arm on which all the wheels are mounted or, indeed, may be formed as two or more separate arms, for example, wheel W1 being mounted on a first arm and wheels W2 and W3 being mounted on a second arm. A preferred example is a single arm on each side, but this is not essential.

A neutral plane 20 is defined and is shown in FIG. 2B. The neutral plane typically passes through an axis 21 on which wheels W3 are mounted. Wheels W3 are pivotable around respective axes 21 so as to change the angle of wheel W3 from the position shown in FIGS. 2B and 2C in which the wheel has its inner edge (the interface 18) below the neutral plane 20 and its outer portion above the neutral plane 20, to a position shown in FIGS. 3B and 3C in which the inner portion (the interface 18) of wheel W3 is above the neutral plane 20. It may be that wheels W2 and or W1 are also capable of being pivoted about the same or a different axis to achieve a similar affect, although in the preferred embodiment only wheel W3 is pivotable in this way.

In FIG. 2B, wheel W2 is shown having a "flower" or "petal" configuration in which the diameter of the wheel is not constant. By this, and as shown in FIGS. 2A and 2D, wheel W2 is provided with a plurality of projections 40 which define regions of the wheel having a large diameter, interspersed by reduced diameter sections 41. Such a configuration of wheel W2 may assist with improved gripping during use. However, such a configuration could be used on any of all of the wheels of the tool 10. Indeed, other forms of wheels are contemplated, including, but not limited to, wheels having a smooth outer edge/interface, a serrated outer edge/interface or a combination thereof.

Wheels W3 are pivotable about axis 21 by virtue of an actuator 50 which is mounted within the hollow shell formed by upstanding wall 30 and base portions 31 and 31a. The actuator 50 is itself movable relative to the main body 11, in this example by pivoting about a pivot line 51, although the movement could include twisting, sliding or any other mechanism which causes part of the actuator to move relative to the wheel or wheels being moved. The actuator is connected to part of a wheel housing 60, in which wheel W3 is mounted. Pivoting of the actuator causes a portion of housing 60 to be raised relative to the neutral plane 20, thereby causing the housing 60 to pivot around axis 21, thereby altering the angle of wheel W3 relative to the remainder of the tool 10. Whilst in this example only wheel W3 is movable in this way, is conceivable that other actuators, or the same actuator, could be provided to move, or change the angle of, wheels, W1 and/or W2.

Indeed, it is worth making clear that, although the example shown in the Figures are provided with three wheels on each side of the channel, the wheels providing the interfaces which engage with the skin, a greater or smaller number of wheels could be provided. In particular 2 or 4 wheel on each arm are envisaged.

As can be seen in the Figures and, in particular, in FIGS. 2B and 3B, the different pairs of wheels are formed at different angles relative to each other.

Various preferred structural features are shown below in table 1 and with reference to FIGS. 4 to 7. In particular, whilst the specific values have been provide for a working example, preferred ranges have been indicated where appropriate. For the avoidance of doubt, any of the material properties and/or measurements, ratios or the like listed in table 1 could be implemented independently of any other feature. Therefore, as an example, if diameter of W1 is 12 mm, table 1 does not make it an explicit requirement that diameter W2 must be 16 mm or diameter W3 be 10.5 mm.

In FIGS. 4 to 7, like elements have been given the same reference numerals.

TABLE 1

| Name | Explanation | Working example | Possible ranges |
|---|---|---|---|
| $\phi_{W1}$ | diameter W1 | 12 mm | 10-16 mm |
| $\phi_{W2}$ | diameter W2 (outer diameter for flower wheels) | 16 mm | 10-20 mm |
| $\phi_{W3}$ | diameter W3 | 10.5 mm | 8-13 mm |
| $\theta_{W1xy}$ | W1 axes angle on xy plane | 160 deg | 90-180 deg |
| $\theta_{W2xy}$ | W2 axes angle on xy plane | 180 deg | |
| $\theta_{W3xy}$ | W3 axes angle on xy plane | 180 deg | |
| $\theta_{W1yz}$ | W1 axes angle on yz plane | 40 deg | 0-120 deg |
| $\theta_{W2yz}$ | W2 axes angle on yz plane | 120 deg | 90-170 deg |
| $\theta_{W3yz}$ | W3 axes angle on yz plane | 120 deg | 110-170 deg |
| $d_{W1}$ | distance between closest point of W1 wheels circumferences on yz plane | 12.55 mm | 6-15 mm |
| $d_{W2}$ | distance between closest point of W2 wheels circumferences on yz plane | 2 mm | 0-3 mm |
| $d_{W3}$ | distance between closest point of W3 wheels circumferences on yz plane | 3.4 mm | 2-4 mm |
| $\alpha_{W1}$ | angle between w1 axis and z axis | 0 | |
| $\alpha_{W2}$ | angle between w2 axis and z axis | 0 | |
| $\alpha_{W3}$ | angle between w3 axis and z axis | 10 | 0-30 |
| $r_{W3}$ | radius of w3 movement (from pivot point to narrower point of w3) | 12.45 mm | 8-20 mm |
| $v_{W3}$ | angle of w3 movement (from down to up position) | 42 deg | 30-45 deg |
| $r_{ss}$ | radius of seesaw movement | 20 mm | |
| $v_{ss}$ | angle of seesaw movement | 24 deg | |
| $\delta$ | ratio for lever arm actuation | 1.5 to 1 | |
| $dx_{W1W2}$ | distance between central point of axes of W1 and W2 on xy plane | 0 mm | |
| $dz_{W1W2}$ | distance between central point of axes of W1 and W2 on xz plane | 14 mm | |

TABLE 1-continued

| Name | Explanation | Working example | Possible ranges |
|---|---|---|---|
| $dx_{W2W3}$ | distance between central point of axes of W3 and W2 on xy plane | 1.75 mm | |
| $dz_{W2W3}$ | distance between central point of axes of W3 and W2 on xz plane | 13.2 mm | |
| F | estimated forces on lateral movement of arms (on xy plane) | | 2-30N |
| E | Moduls of elasticity of material used for the body | | 2.5-3 Mpa ± 1 Mpa |
| Assumptions | | | |
| Implant shape | | cylinder | |
| Implant lengths | | 40 mm | |
| Implant diameter | | 2 mm | |
| Implantation depth (assumed) | | 1 mm | 0.2-5 mm |

Table 1 defines some preferred values for one example of a working device in line with the invention are broad said to define a number of ranges which could be used depending upon different factors. For example, the looseness or tightness of a subject skin may affect the preferred width of the channel and or wheel diameter. The channel width or wheel diameter may also be altered depending upon the amount of sub-dermal fat which a subject has. As such, differing devices having different wheel sizes and or channel widths could be provided.

The tool 10 is provided with an incision guide 70 which, in the example shown, is located in the actuator 50. The incision "70" could be located in the separate element to the actuator 50. The incision guide 70 is intended to assist a user of the device in moving a cutter implement such as a scalpel so as to cut the skin of a user in order to release the implant from beneath the skin. The end of actuator 50 which effectively forms the closed end of channel 16 may also act as a lip which engages with, via the skin, one end of an implant located beneath the skin, so as to raise that end of the implant in order to facilitate its removal. This may be further facilitated by the pivoting action of the actuator 50 which not only raises wheel housing 60, but also acts upon the end of the implant to raise it further, thereby making it easier to identify the end of the implant and therefore make an incision at the appropriate position in the skin. Preferably, the lip is a ramp.

Figure 9:
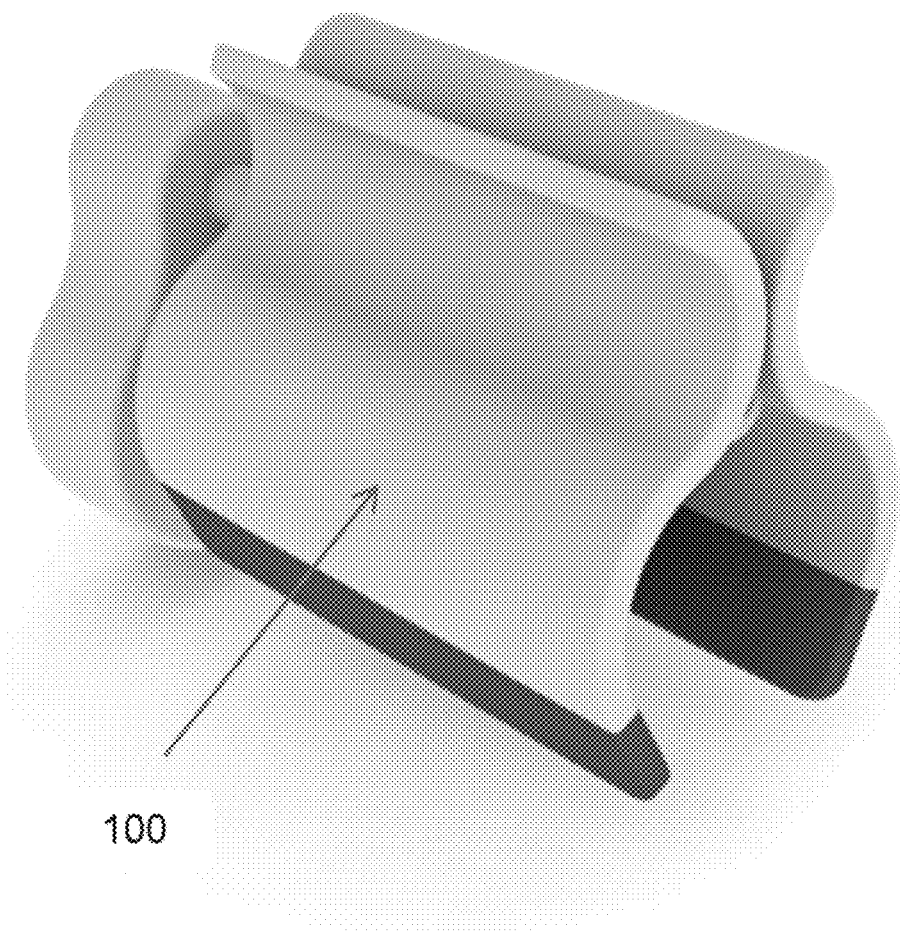
FIG. 9 illustrates an embodiment of an implant removal tool with two pivotable arms that form a channel.

FIG. 9 shows another embodiment of the present invention. A tool is shown, which comprises two pivotable arms (100). The pivotable arms can be used to engage with an implanted item and overlying skin. This allows the position of the implant to be fixed, and the point of incision to be determined. In the embodiment shown in FIG. 9, a channel with a continuous circumference is pre-formed in the main body. In use, i.e. on engagement with the skin, this channel has a discontinuous circumference.

Figure 10:
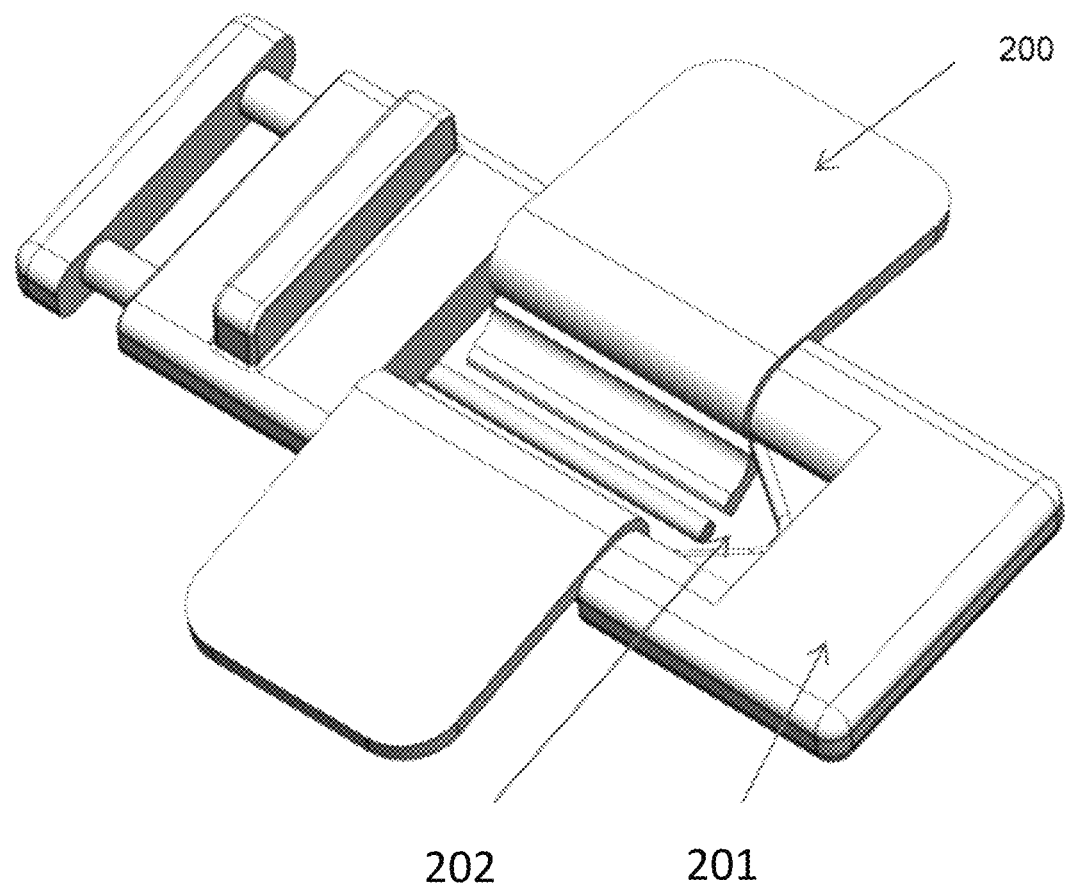
FIG. 10 illustrates another embodiment of an implant removal tool having a main body with a closed channel and a pair of pivotable arms that engage the implanted item through the closed channel.

FIG. 10 shows a further embodiment of the present invention. A tool is shown, which comprises a main body (201), comprising a closed channel (202), i.e. a channel with two closed ends, within the main body. The channel is positioned over the implanted item and the overlying skin. A pair of pivotable arms (200) are then used to engage the implanted item and the overlying skin.

This allows the position of the implant to be fixed, and the point of incision to be determined.

The invention will now be illustrated with reference to the following Example

The following surgical procedure was devised, for using with a tool described in FIGS. 1A to 7. The surgical procedure is a preferred embodiment of a method of the invention.

Surgical Procedure, Sterile Technique:
1. Clean skin using cleaning agent such as Chlorhexidine (or other commonly used antiseptic agents), leave to dry prior to proceeding.
2. Palpate the subdermal implant (optionally mark both ends of the subdermal implant with a skin marker pen).
3. By use of the Device, place front wheels down on skin approximately 0-10 mm distance away from the tip of the implant (either end of the implant may be used), holding the device at an angle of approximately 5-50 degrees to the skin.
4. Move the device forward at the same time as the angle of the device to the skin is reduced, ensuring by visual means that the implant is gripped by the second and thereafter the third set of wheels as the device is moved along the length of the implant. Continue until the tip is located at least past the back wheels.
5. Use the "lever" to lift the two back wheels gripping the implant in order to lock the implant into place. This will provide a secure platform on which to perform the surgical procedure.
6. Use the "track" in the lever to ensure correct position of injection of local anaesthetic beneath the implant.
7. Give the local anaesthetic at least 1 minute to work. Thereafter, use the "track" in the lever to guide a scalpel to the point of incision (i.e. where the tip of the scalpel meets the skin.
8. Incise the skin using a firm movement of the scalpel blade forwards and upwards from the point where it touches the tip of the implant.
9. The implant should now be exposed inside the incision, and may be protruding through the incision. If protruding, use fingers (sterile gloved) or a pair of forceps to remove the implant. If the implant is visualised, but not protruding, ensure that any fibrin sheath that may be encapsulating the implant is incised prior to attempting further removal. Use a pair of forceps to extract the implant through the incision. It may be necessary to push the implant down through the middle set of wheels in order to extract the implant through the incision.
10. Once the implant is extracted, the "lever" is lowered, and the device pulled backwards (opposite direction to initial engagement) until it is free from the skin.
11. Close the incision using steristrips and a sterile bandage. If another implant is to be inserted, this may be done after step 10. Insertion should be done through the incision made during removal.
12. The device should be disposed of as biohazardous material after use.

The above surgical procedure was tested on a patient. The procedure successfully removed the implant in a reduced amount of time compared to known procedures, and minimum bruising was observed initially.

The invention claimed is:

1. A method for removing an elongate rod implanted beneath a skin surface, the elongate rod having a longitudinal extent aligned generally parallel to the surface of the skin, the method comprising the steps of:
- locating the elongate rod beneath the skin surface;
- positioning the elongate rod with an implant removal tool comprising:
  - at least two arms moveable relative to each other;
  - at least two gripping interfaces on each arm; and,
  - an elongate slot between the at least two arms, wherein the elongate slot defines a width that maintains a separation between the at least two gripping interfaces on the arms when the arms are at rest, the width being adjustable by at least one of moving the arms further apart and moving the arms closer together;
- placing the at least two arms along the longitudinal extent on each side of the implanted elongate rod, so that the at least two gripping interfaces on the arms are on each side of the implanted elongate rod;
- moving at least one arm so that the gripping interfaces are beneath the implanted elongate rod, whereby the implanted elongate rod is supported by the at least two arms above the gripping interfaces, thereby fixing the position of the implanted elongate rod under the skin and causing the skin beneath the implanted elongate rod to be pinched within the elongate slot, wherein the width of the elongate slot inhibits the skin therein from being damaged;
- making an incision in the stretched skin to expose a part of the implanted elongate rod;
- engaging the exposed part of the implanted elongate rod; and,
  - removing the elongate rod from beneath the surface of the stretched skin through the incision.

2. The method of claim 1, further comprising deploying a scalpel integral with the implant removal tool and making the incision with the scalpel.

3. The method according to claim 1, wherein the elongate rod is a contraceptive implant.

4. The method of claim 1, further comprising locking a position of the gripping interfaces after moving at least one arm.

5. The method of claim 1, further comprising injecting a local anaesthetic.

6. A method for removing an elongate rod which has been subcutaneously or subdermally implanted in a human body beneath a surface of the skin, the elongate rod having a longitudinal extent aligned generally parallel to the surface of the skin, the method comprising the steps of:
- securing the elongate rod along the longitudinal extent using an implant removal tool having at least two gripping interfaces which are moveable relative to each other to engage the skin along opposite sides of the elongate rod thereby to secure the elongate rod in a raised position relative to the gripping interfaces;
- deploying a scalpel integral with the implant removal tool to make an incision in the skin overlying the elongate rod; and,
- removing the elongate rod from the human body through the incision.

7. The method of claim 6, wherein the implant removal tool comprises two arms, each arm comprising at least two gripping interfaces,
and wherein securing the contraceptive rod comprises positioning one arm on each side of the contraceptive rod and moving at least one arm such that the gripping interfaces engage the skin around the contraceptive rod, thereby stretching the skin around the contraceptive rod.

8. The method of claim 6, further comprising locking a position of the gripping interfaces after securing the contraceptive rod.

9. The method of claim 6, wherein the tool further comprises a slot between the two arms, wherein the slot defines a width that maintains a separation between the gripping interfaces on the arms when the arms are at rest, the width being adjustable by at least one of moving the arms further apart and moving the arms closer together.

10. The method of claim 6, further comprising injecting a local anaesthetic.

* * * * *